United States Patent [19]

Vadgama et al.

[11] Patent Number: 5,437,973
[45] Date of Patent: Aug. 1, 1995

[54] ENZYME-ELECTRODE SENSOR

[75] Inventors: Pankaj M. Vadgama, Newcastle-Upon-Tyne; Stephen Churchouse, Gateshead; William Mullen, Newcastle-Upon-Tyne, all of England

[73] Assignee: The Victoria University of Manchester, United Kingdom

[21] Appl. No.: 58,037

[22] Filed: May 7, 1993

Related U.S. Application Data

[63] Continuation of Ser. No. 636,560, Jan. 7, 1991, abandoned, which is a continuation of Ser. No. 188,189, May 2, 1988, abandoned, which is a continuation of Ser. No. 909,491, Sep. 16, 1986, abandoned.

Foreign Application Priority Data

Sep. 16, 1985 [GB] United Kingdom ............ 8522834

[51] Int. Cl.$^6$ ............. C12N 1/34; G01N 27/327
[52] U.S. Cl. ........................... 435/4; 435/288; 435/817; 204/403; 204/415
[58] Field of Search .......... 435/4, 11, 14, 288, 435/291, 817; 422/80, 82.01; 436/63, 68, 151; 204/153, 12, 403, 409, 415

[56] References Cited

U.S. PATENT DOCUMENTS

| | | | |
|---|---|---|---|
| 3,539,455 | 2/1970 | Clark . | |
| 3,723,064 | 3/1973 | Liotta | 422/56 X |
| 3,979,274 | 9/1976 | Newman . | |
| 4,066,403 | 1/1978 | Bruschi | 436/71 X |
| 4,240,438 | 12/1980 | Updike et al. | 128/635 |
| 4,356,074 | 10/1982 | Johnson | 435/817 X |
| 4,388,166 | 6/1983 | Suzuki et al. | 435/817 X |
| 4,401,122 | 8/1983 | Clark | 128/635 |
| 4,418,148 | 11/1983 | Oberhardt | 435/288 X |
| 4,442,821 | 4/1984 | Uehara et al. | 128/635 |
| 4,522,786 | 6/1985 | Ebersole | 422/57 X |
| 4,919,767 | 4/1990 | Vadgama et al. | 435/288 X |

FOREIGN PATENT DOCUMENTS

| | | |
|---|---|---|
| 59-164953 | 9/1984 | Japan . |
| 60-185153 | 9/1985 | Japan . |
| 60-185155 | 9/1985 | Japan . |
| 63-145447 | 7/1986 | Japan . |

OTHER PUBLICATIONS

Patent Abstracts of Japan, vol. 10, No. 344 (P-518)(2400) 20th Nov. 1986; and JPA 61 145 447 (Fuji Electric Co. Ltd.) 03 Jul. 1986.
Patent Abstracts of Japan, vol. 10, No. 38 (P-428)(2095), 14 Feb. 1986; and JPA 60 185 153 (Fuji Denki Sougou Kenkyusho) 20 Sep. 1985.
Patent Abstracts of Japan, vol. 9, No. 16 (P-329) (1739) Jan. 23, 1985; and JPA 58 38315 (Fuji Denki Sougou Kenkyusho K.K.
Clark and Lyons, Annals of The New York Academy of Science, 102, 29–45, 1962.
Clinics In Perinatology, vol. 12, No. 1, Feb. 1985; Joyce L. Peabody et al "Noninvasive Monitoring Of Blood Gases In The Newborn"—Historical Background; pp. 147–160.

Primary Examiner—Jeffrey R. Snay
Attorney, Agent, or Firm—Cushman, Darby & Cushman

[57] ABSTRACT

A sensor of the enzyme-electrode type containing a layer of porous material of restricted permeability between the enzyme and a sample to be analysed. The porous material has a percentage porosity not greater than 5% and preferably in the range 0.005% to 0.5%.

7 Claims, 3 Drawing Sheets

ENZYME-ELECTRODE SENSOR

This is a continuation of application Ser. No. 07/636,560, filed on Jan. 7, 1991, which was abandoned upon the filing hereof; which is a continuation of application Ser. No. 07/188,189 filed May 2, 1988, now abandoned; which is a continuation of application Ser. No. 06/909,491 filed Sep. 16, 1986, now abandoned.

BACKGROUND OF THE INVENTION

1. Field of the Invention

This invention relates to a sensor of the enzyme electrode type comprising an improved membrane and to an analytical method using the sensor.

2. Description of the Related Art

Enzyme electrodes are increasingly used in medical and other laboratories particularly for the determination of materials such as glucose and urea in specimens of blood and other physiological fluids. Such electrodes are described in many publications notably an article by Clark and Lyons (Annals of the New York Academy of Science, 102, 29–45, 1962) and U.S. Pat. Nos. 3,539,455 and 3,979,274 to Clark and Newman respectively. Enzyme electrodes are generally used to determine materials which themselves are not electrochemically active but which in the presence of suitable enzymes take part in reactions which produce species which can be readily detected by the electrodes. In enzyme electrodes the enzymes are frequently located within polymeric materials in close proximity to the underlying electrode.

A considerable amount of research has been carried out in order to improve the properties of membranes for use in enzyme electrodes and many membranes for this purpose have been disclosed. An example of a type of membrane which is often used is the laminated membrane disclosed by Newman in U.S. Pat. No. 3,979,274. This membrane comprises a first or inner layer of an essentially homogeneous material, for example cellulose acetate, which can prevent the passage of materials of low molecular weight likely to interfere with the enzymic signal, a close adherent layer of the enzyme itself (with or without such other materials that may be blended with it), and a second layer (in this instance an outer layer) of a porous support film which can prevent the passage of cellular and colloidal elements.

The determination of glucose can be taken as an example of the determination of a material by an enzyme electrode. In the presence of the enzyme glucose oxidase the following reaction occurs:

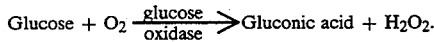

Glucose + O$_2$ $\xrightarrow{\text{glucose oxidase}}$ Gluconic acid + H$_2$O$_2$.

The hydrogen peroxide produced in this reaction passes through the first layer of a membrane such as that of U.S. Pat. No. 3,979,274 and can be determined using the electrode. Since the hydrogen peroxide produced is dependent upon the glucose present in a specimen, the glucose concentration can be determined using a suitably calibrated sensor.

To date a number of difficulties have limited the utility of enzyme electrodes and restricted the scale of their use in routine analysis of, e.g. blood samples. Significant among these difficulties is the limited linearity of the response of electrodes to analytes such as glucose or lactate which are substrates for the enzyme catalysed reactions. The response is linear only over a limited range of low concentrations of the analytes and hence the concentrations of the materials to be determined must be low and generally diluted samples must be used in specimens for analysis using enzyme electrodes. It is not always practicable to make diluted samples for routine analysis outside the laboratory and it would be impossible for invasive monitoring.

SUMMARY OF THE INVENTION

According to the present invention we provide a sensor of the enzyme—electrode type for the determination of an analyte, said analyte being convertable in the presence of an enzyme into a species which can be detected by the sensor, which comprises an electrode and a membrane permeable to liquids and solutes positioned between the electrode and a specimen containing the analyte, said membrane comprising a layer containing one or more enzymes and a layer of material positioned between the enzyme—containing layer and the specimen characterised in that said layer of material contains an area through which analyte can pass formed from a porous material of restricted permeability having a porosity which is not greater than 5%.

Further according to the invention we provide a method for determining an analyte in a specimen when comprises contacting the specimen with the outer layer of a membrane, permeable to liquids and solutes and comprising one or more enzymes, in the presence of which the analyte is convertable into a species detectable by a sensor which incorporates the membrane, and one or more layers of material, and measuring the response of the sensor to the species, characterised in that a layer in the membrane between the enzyme and the specimen contains an area through which analyte can pass formed from a porous material of restricted permeability having a porosity which is not greater than 5%.

The area formed from a porous material having a porosity which is not greater than 5% causes the layer containing it to have restricted permeability. Preferably all or a major proportion of the effective area of this layer is formed from material having a porosity which is not greater than 5%.

DETAILED DESCRIPTION OF THE PREFERRED EMBODIMENTS

Figure 1:
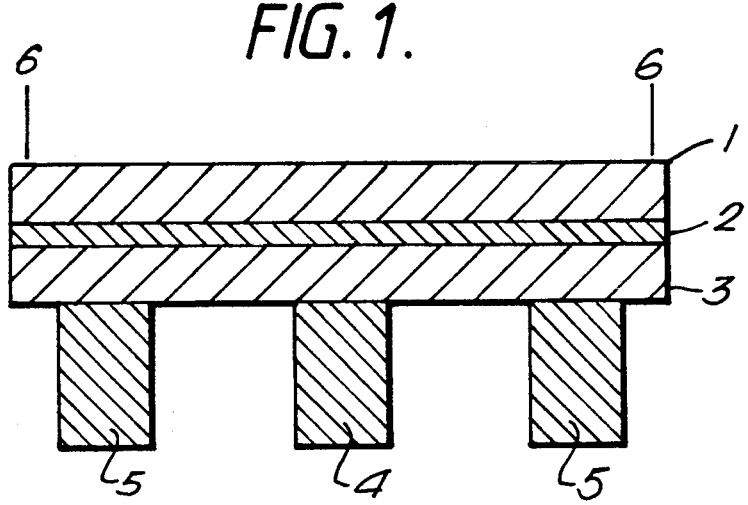
FIG. 1 is a schematic cross-sectional view of sensor provided in accordance with the present invention.

In its most simple form the membrane in the sensor of the invention consists of the enzyme—containing layer and the layer of restricted permeability. The layer of restricted permeability is the outer layer in this simple form of membrane and is contacted directly by the specimen in the method of the invention for determining an analyte.

However it is preferred that the membrane is a laminated membrane of the type of which that disclosed in U.S. Pat. No. 3,979,274 is an example. Such a membrane comprises a first or inner layer of material positioned between the enzyme-containing layer and the electrode, the enzyme-containing layer and a second layer of material on the other side of the enzyme-containing layer which second layer is the layer having restricted permeability.

Hereafter in this specification the sensor of the invention which is described will contain a laminated membrane of the type of which the membrane described in U.S. Pat. No. 3,979,274 is an example having first and second layers the layer comprising the porous material having restricted permeability being the second layer.

It should be understood that the membranes in the sensor of the invention can contain more than two layers of material in addition to the enzyme-containing layer. For instance the second layer, i.e. of restricted permeability, is not necessarily the outermost layer of the membrane. There may be a further layer or layers of material, i.e. third, fourth etc layers, between the second layer or layer of restricted permeability and the specimen. Often however the second layer will be the outer layer and its outer face will be contacted by the specimen.

Generally the porous material of restricted permeability uysed in the second layer will be a polymeric material but other suitable materials may be used. Thus the second layer may be formed from glass or a metal having pores cut by lasers.

Suitably the second layer of material is formed from material having a porosity not greater than 2%. Very low porosities are preferred for instance in the range 0.001% or 0.005% to 0.5%.

Percentage porosity is the product of pore area X pore density X100. Most suitable porous materials of low percentage porosity will have pores of mean diameter less than 0.03 microns, preferably 0.01 to 0.03 microns. However materials having pores of mean diameter greater than 0.03 microns can be used successfully if the pore density is reduced. Thus materials having mean pore diameters up to 0.2 microns can be used. Examples of rated pore size and rated pore densities for materials of suitable low porosities are as follows:

| Rated Pore Size (microns) | Rated Pore Density (pores/cm$^2$) | Calculated % Porosity |
| --- | --- | --- |
| 0.1 | $3 \times 10^8$ | 2.3 |
| 0.05 | $6 \times 10^8$ | 1.1 |
| 0.03 | $6 \times 10^8$ | 0.42 |
| 0.01 | $6 \times 10^8$ | 0.047 |
| 0.01 | $1 \times 10^8$ | 0.008 |

Other material parameters which may be manipulated to produce material of suitably restricted permeability for the second layer of porous material include pore tortuosity. The thickness of the second layer also influences permeability.

In the sensor of the invention the second layer of the membrane acts as a diffusion barrier and prevents or restricts the passage of compounds of high molecular weight and gives strength to the membrane sufficient to enable it to retain its shape and to maintain suitable contact with the electrode. Suitable porous materials for the second layer include porous polycarbonates, polyurethanes, and modified cellulose particularly cellulose nitrate, cellulose acetate and regenerated cellulose.

Suitable materials also include materials having molecular weight cut-offs of 20,000 or less. To ensure rapid electrode responses the thickness of the second layer is preferably less than 20 microns, especially in the range 1 to 10 microns. Especially suitable materials for the second layer have pores of mean diameter within the range 0.015 microns to 0.025 microns.

The sensor of the invention may have a detachable membrane or it may be a disposable sensor with an adherent membrane. Materials used in the formation of suitable electrodes for the sensors include inert metals and/or carbon.

When the sensor incorporates a laminated membrane of the type disclosed in U.S. Pat. No. 3,979,274 the first layer which is to be located between the enzyme layer and the electrode is suitably formed from polymethylmethacrylate, polyurethane, cellulose acetate or another porous material which will restrict or prevent passage of electroactive interfering compounds such as ascorbic acid and tyrosine. Suitably the first layer has a thickness in the range 0.2 microns to 1.0 microns.

The enzyme present in the sensor of the invention may be located in the membrane in any suitable manner. Preferably in a laminated membrane it is present between the first and second layers of porous material and forms the bond between them. In this situation, and also generally, the enzyme is preferably immobilised by mixing with a material which causes cross linking to occur. A very suitable material for this purpose is glutaraldehyde; proteins such as albumin and other materials may also be included. In order to facilitate the obtaining of rapid stable readings from the sensor it is preferred that the enzyme-containing layer is thin, i.e. not greater than 5 microns thick.

The enzyme to be used in the sensor of the invention will depend upon the analyte whose concentration is to be determined. If the analyte is glucose then the enzyme will be for example glucose oxidase. Other enzymes which may be present include uricase and lactate oxidase for determination of uric acid and lactic acid respectively. Enzyme systems comprising two or more enzymes may also be present.

A laminated membrane for use in the sensor of the invention for the determination of glucose may be prepared by a method including the following steps:

1. 1 mg glucose oxidase is dissolved in 50 $\mu$l of (100 mg/ml) albumin:

2. 3 $\mu$l of 12.5% glutaraldehyde solution is mixed with 3 $\mu$l of the enzyme/albumin mixture on a glass microscope slide:

3. 1 $\mu$l of the mixture produced in the previous step is applied to one face of a 1 cm$^2$ polycarbonate film having a porosity not greater than 5% and pores with a mean diameter below 0.03 microns:

4. The other surface of the enzyme layer is covered immediately with a thin cellulose acetate film and the resulting laminated membrane is clamped for 3 minutes between glass slides. After removal from the glass slides the laminated membrane produced by the above sequence of steps may be applied to a platinum electrode to form the sensor of the invention, the cellulose acetate film being nearest to the electrode and forming the first layer.

Use of the method of the invention gives the advantage of an increase in the concentration range over which a graph of concentration against sensor response is linear. With conventional methods linearity was generally extended only up to approximately a concentration of 3 m mol per litre for glucose. Using the method of the invention linearity is increased and the range extends to glucose concentrations of 50 m mol per litre and even higher. At the higher concentrations this is achieved through restriction of substrate entry into the enzyme layer and therefore with some loss of sensitivity. Thus the range covers the concentrations of glucose which can be anticipated in blood samples thereby enabling blood glucose levels to be determined more readily. This is a considerable advantage in situations where large numbers of determinations must be made regularly and with minimal sample preparation. Linearity is also extended by applying to the second layer of the membrane a medium comprising an organo-silane having reactive groups as described in our co-pending European Patent Application No. 86303907.9. This treatment may be applied to the second layer of the membrane in the sensor of the present invention to produce a combined effect and further improved linearity.

The invention is illustrated by FIG. 1 of the accompanying drawings.

In FIG. 1, reference numeral 1 is the second layer of the membrane formed from a polycarbonate film having a porosity of 0.42%, 2 is a layer of glucose oxidase enzyme dissolved in albumin and mixed with glutaraldehyde, 3 is the first layer formed from cellulose acetate, 4 is the platinum working electrode and 5 is the silver reference electrode. 1, 2 and 3 together form a laminated membrane. Platinum working electrode 4 acts as an anode whilst silver reference electrode 5 acts as a cathode. The membrane is held in place on the electrode by a perspex ring pressing down on outer layer 1 towards its outer edges at 6.

The use of the sensor shown in FIG. 1 is illustrated in the following examples:

EXAMPLE 1

An aqueous solution containing 30 mg/ml glucose oxidase enzyme (E.C.1.1.3.4) and 200 mg/ml albumin was mixed with an equal volume of a solution containing 50 µg/ml glutaraldehyde. A 1 cm$^2$ piece of a "NUCLEPORE" polycarbonate film (mean pore diameter=0.05 microns) was exposed to 5 µl of the mixed solutions in order to impregnate the film with the enzyme. In this instance the film acts as a support for the enzyme and has no effect on the linearity of the response obtained from the sensor.

The enzyme-impregnated film was placed over the working and reference electrodes of the sensor (which had previously been moistened with 0.067M phosphate buffer containing 50 m mol per litre sodium chloride at pH 7.4 to ensure electrolytic contact between the working and reference electrodes). The film to be studied as the second layer was placed over the enzyme impregnated film. The screw-fit top of the electrode body was then positioned and tightened putting slight tension on the resulting laminated membrane. The membrane was then tested. Since the upper film (the film to be be tested as the second layer) may be replaced with other films, it was possible to use the same supported enzyme layer for several different second layers).

In this example the films tested as the second layer were as follows:

(1) A further 0.05 micron mean pore diameter "NUCLEPORE" polycarbonate film:

(2) A 0.015 micron mean pore diameter "NUCLEPORE" polycarbonate membrane; and (3) A regenerated cellulose film made by Schleicher and Schull (RC52) having a mean pore diameter of 0.01 microns.

Figure 2:
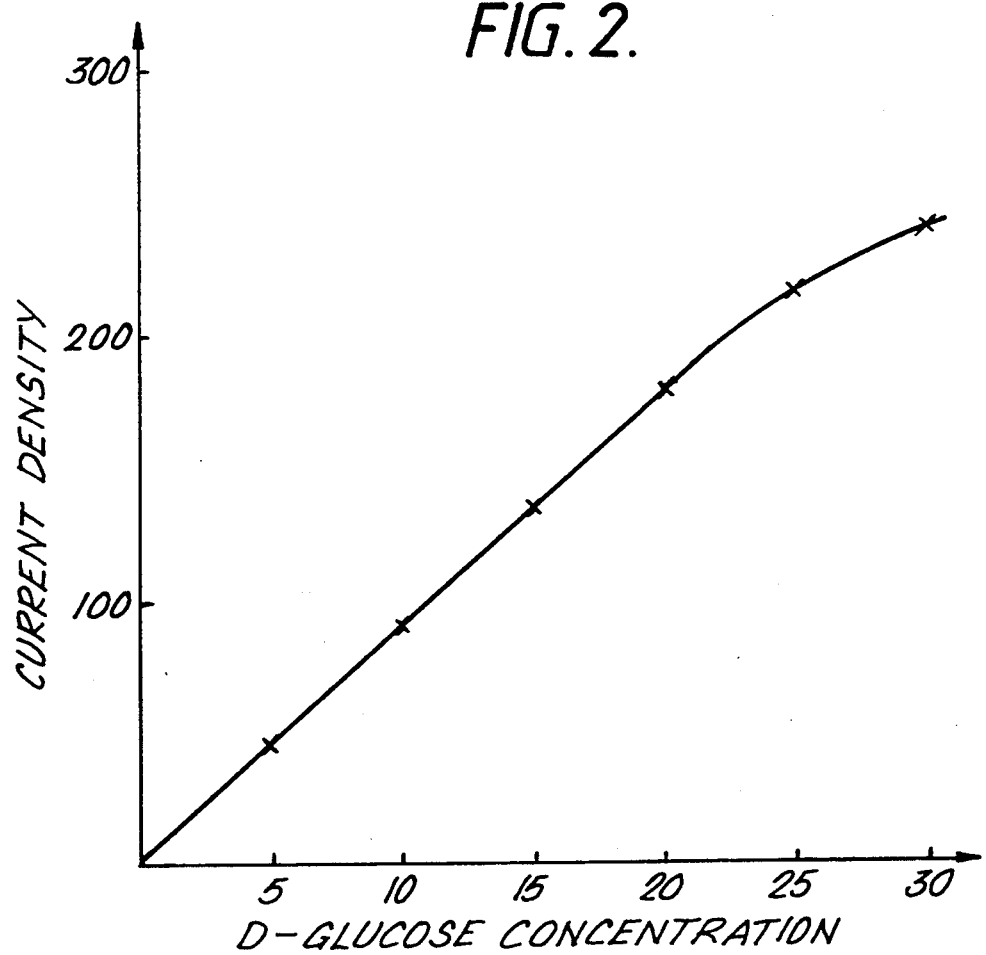
FIG. 2 is a graph of current density in μA against glucose concentration in M mol. per liter for film 2 of Example 1.
Figure 3:
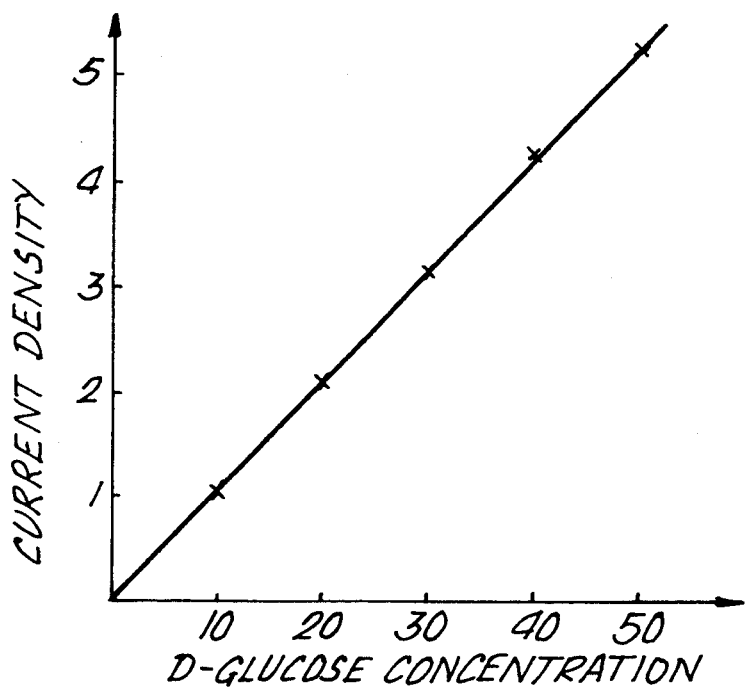
FIG. 3 is a graph of current density in μA against glucose concentration in M mol. per liter for film 3 of Example 1.

With film (1) the linearity of the sensor was 7 m mol per litre. The results with films (2) and (3) are given in FIGS. 2 and 3 respectively of the accompanying drawings which are graphs of current density in µA (ordinates) against glucose concentration in m mol per litre (abcisses). These show that, using films (2) and (3) as the second layer, the sensor shows much greater linearity—greater than 20 m mol per litre for (2) and at least 50 m mol per litre for (3). Response time (98%) for (2) was 30–60 seconds and for (3) 20 minutes. Response time (90%) for (3) was 7 minutes.

EXAMPLE 2

Example 1 was repeated with a lactate oxidase enzyme (E.C.1.1.3.2.). The films tested as the second layer were those described as (1) and (2) in Example 1, having mean pore diameters of 0.05 microns and 0.015 microns respectively.

Figure 4:
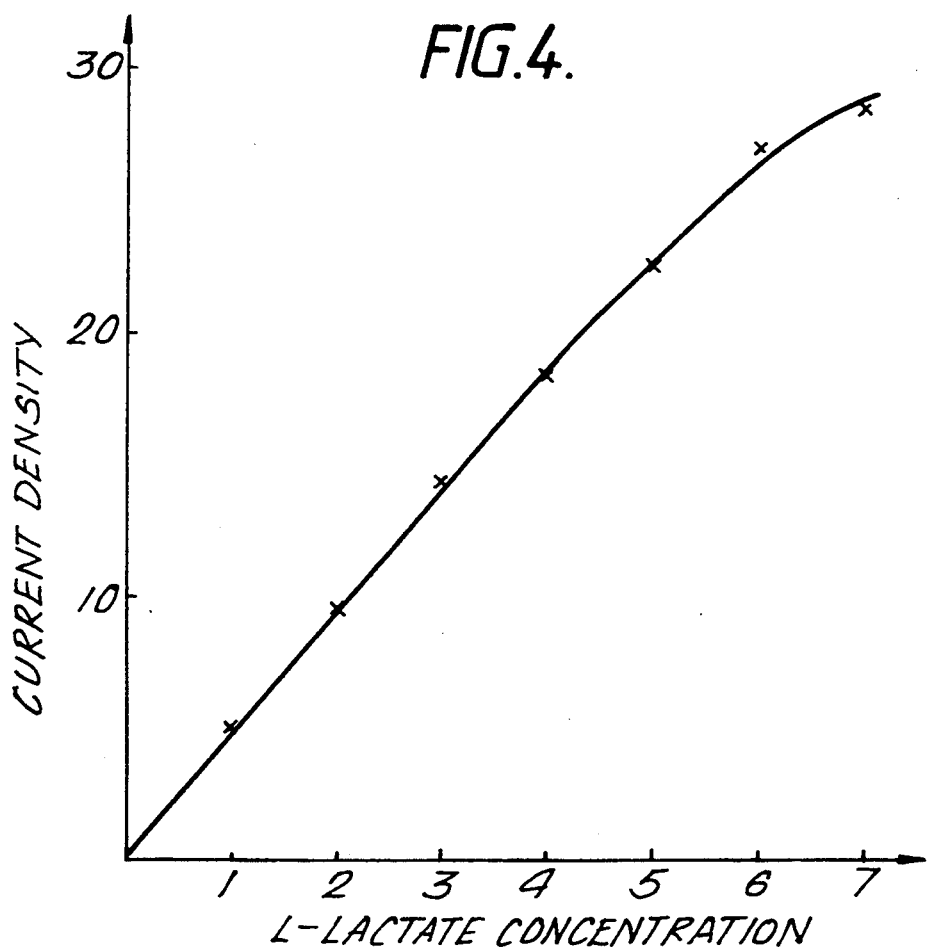
FIG. 4 is a graph of current density in μA against glucose concentration in M mol. per liter for film 2 of Example 2.

With film (1) the linearity of the sensor was 0.2 m mol per litre. The result with film (2) is shown in FIG. 4 of the accompanying drawings which is a graph of current density in µA (ordinate) against glucose concentration in m mol per litre (abcissa). Again linearity using the smaller pore film as the second layer is much greater than when the larger pore film is used. In this instance a linearity of at least 4 m mol per litre is achieved with film (2), the response time being 1–2 minutes.

EXAMPLE 3

Figure 5:
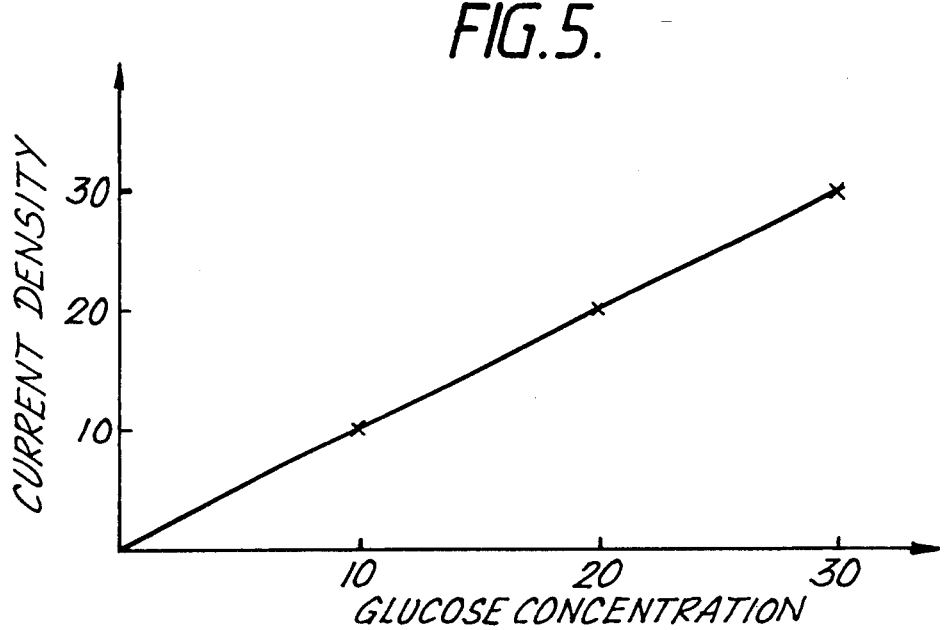
FIG. 5 is a graph of current density in μA against glucose concentration in M mol. per liter for Example 3.

The method of Example 1 was used to test as the second layer a regenerated cellulose film made by Schleicher and Schull (RC52) having a designated pore size in the range 0.005 to 0.010 µm. The result is shown in FIG. 5 which is a graph of current density in µA (ordinate) against glucose concentration in m mole per litre (abcissa). This shows that the response of the sensor is linear over a substantial concentration range.

EXAMPLE 4

Figure 6:
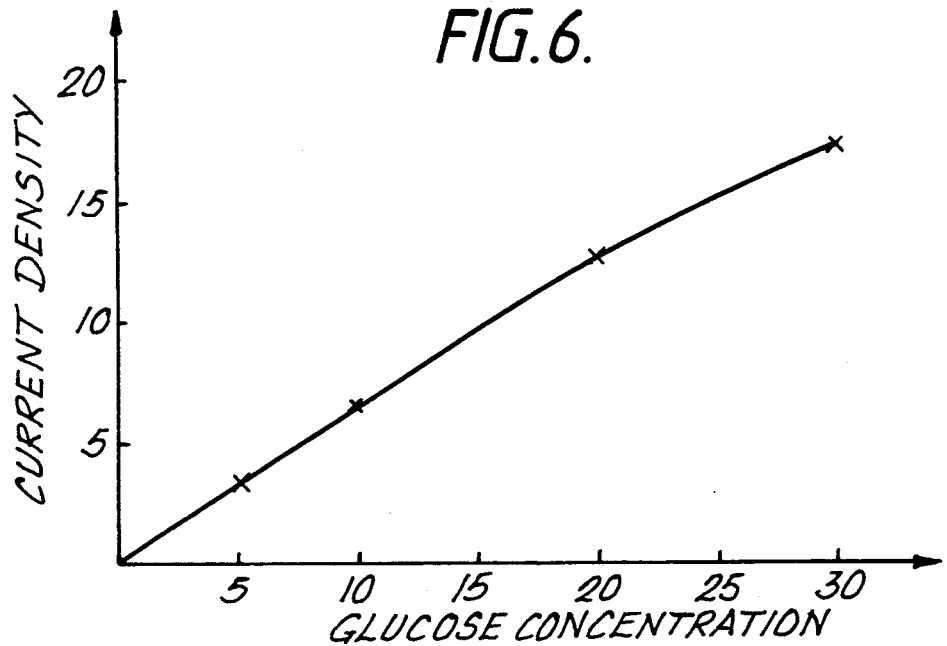
FIG. 6 is a graph of current density in μA against glucose concentration in M mol. per liter in respect to Example 4.

The method of Example 1 was used to test as the second layer a cellulose acetate film made by Schleicher and Schull (AC62) having a designated pore size in the range 0.005 to 0.01 µm. The result is shown in FIG. 6 which is a graph of current density in µA (ordinate) against glucose concentration in m mol per litre (abcissa). This shows that the response is linear over a substantial concentration range.

We claim:

1. An enzyme-electrode sensor for determining an analyte, which analyte is converted by an enzyme into a species detectable by the sensor, said sensor comprising:

an electrode; and a membrane, superimposed on said electrode in physical contact therewith, said membrane being permeable to liquids and solutes, and wherein said membrane further comprises a first layer containing at least one enzyme, and a second layer, disposed on that side of the first layer which is further from said electrode, which second layer includes an area of porous material of restricted permeability through which the analyte can pass and has a porosity within a range of 0.001 to 0.5 percent and a mean pore diameter that does not exceed 0.01 microns.

2. An enzyme-electrode sensor according to claim 1, wherein said membrane comprises in addition an inner layer, disposed between said first layer and said electrode.

3. An enzyme-electrode sensor for determining an analyte, which analyte is converted by an enzyme into a species detectable by the sensor, said sensor comprising:
   an electrode; and
   a membrane permeable to liquids and solutes, positioned in physical contact with the electrode, said membrane comprising at least:
   a) a first layer,
   b) a second layer overlying and contacting said first layer and disposed on a side of said first layer farther from said electrode, and
   c) an inner layer underlying said first layer,
   wherein said first layer contains at least one enzyme,
   wherein said second layer has a porosity lying within the range of 0.001 to 0.5 percent and wherein a mean pore diameter does not exceed 0.01 microns and is selected from the group consisting of polycarbonates, polyurethanes and modified cellulose; and
   wherein said inner layer is disposed between said first layer and said electrode and comprises a porous material of a type which restricts or prevents the passage of electroactive interfering compounds.

4. An enzyme-electrode sensor according to claim 3 wherein said inner layer comprises a polymeric material selected from the group consisting of polymethyl methacrylate, polyurethane and cellulose acetate.

5. A method for determining an analyte in a specimen, which comprises the steps of:
   contacting a specimen to be determined with a membrane which is permeable to liquids and solutes and comprises at least two layers, a first of which layers comprises at least one enzyme, which convert the analyte into a species detectable by an electrode sensor, and a second of which layers, disposed between said first layer and the specimen to be analyzed, contains an area through which analyte can pass, formed from a porous material of restricted permeability having a porosity lying within the range 0.001 to 0.5 percent and a mean pore diameter no more than 0.01 microns;
   detecting said species by said sensor; and
   measuring a response of said electrode sensor to said species to determine the concentration of said analyte in the specimen.

6. An enzyme-electrode sensor for determining an analyte, which analyte is converted by an enzyme into a species detectable by the sensor, said sensor comprising:
   an electrode; and
   a membrane permeable to liquids and solutes, positioned in physical contact with the electrode, said membrane comprising at least:
   a) a first layer,
   b) a second layer overlying and contacting said first layer and disposed on a side of said first layer further from said electrode, and
   c) an inner layer underlying said first layer,
   wherein said second layer has a porosity such that it has a restricted permeability, and is formed from a material selected from the group consisting of polycarbonates, polyurethanes and modified cellulose, and wherein said second layer has a porosity in the range of from 0.001 to 0.05 percent and a mean pore diameter no larger than 0.01 microns; and
   wherein said inner layer is disposed between said first layer and said electrode and comprises a porous material of a type which restricts or prevents the passage of electroactive interfering compounds and wherein said first layer includes at least one enzyme immobilized beneath the second layer.

7. An enzyme-electrode sensor according to claim 6, wherein the enzyme is immobilised within a layer between the second layer and the inner layer and also within the pores of the inner layer.

* * * * *